US005593508A

United States Patent [19]
Gatt et al.

[11] Patent Number: 5,593,508
[45] Date of Patent: Jan. 14, 1997

[54] MOIST, ABSORBENT MATERIAL FOR CLEANING ARTICLES AND SURFACES

[75] Inventors: Shimon Gatt; Yechezkel Barenholz; Herve Bercovier, all of Jerusalem; Zvi Eldar, Haifa, all of Israel

[73] Assignee: Yissum Research Development Company of the Hebrew University of Jerusalem, Jerusalem, Israel

[21] Appl. No.: 364,587

[22] Filed: Dec. 27, 1994

Related U.S. Application Data

[63] Continuation-in-part of Ser. No. 13,846, Feb. 5, 1993, Pat. No. 5,376,183, which is a continuation-in-part of Ser. No. 653,319, Feb. 11, 1991, Pat. No. 5,401,413.

[51] Int. Cl.[6] .................. A61K 7/50; D04H 1/58
[52] U.S. Cl. .................. 134/40; 428/291; 134/42
[58] Field of Search .................. 210/610; 134/25.1, 134/25.5, 38–40, 42; 428/288, 289, 249, 291; 206/205, 210

[56] References Cited

U.S. PATENT DOCUMENTS

| | | | |
|---|---|---|---|
| 4,087,356 | 5/1978 | Marconi et al. | 210/922 |
| 4,146,470 | 3/1979 | Mohan et al. | 210/422 |
| 4,230,562 | 10/1980 | Olivieri et al. | 210/610 |
| 4,284,509 | 8/1981 | Lindorfer et al. | 210/922 |
| 4,382,873 | 5/1983 | Gatellier et al. | 210/610 |
| 4,414,333 | 11/1983 | Olivieri et al. | 210/610 |
| 4,462,910 | 7/1984 | Lepain et al. | 210/610 |
| 4,623,468 | 11/1986 | Lepain et al. | 210/922 |
| 4,749,080 | 6/1988 | Toohey | 206/210 |
| 4,753,844 | 6/1988 | Jones et al. | 428/288 |
| 4,811,791 | 3/1989 | Harnoy et al. | 166/305.1 |
| 4,822,490 | 4/1989 | Dyadechko et al. | 210/922 |
| 4,998,984 | 3/1991 | McClendon | 206/205 |
| 5,019,174 | 5/1991 | Wallach | 134/40 |
| 5,256,417 | 10/1993 | Koltisko | 428/249 |
| 5,320,217 | 6/1994 | Lenarz | 206/210 |

FOREIGN PATENT DOCUMENTS 2172796  5/1973  France.

OTHER PUBLICATIONS

"Lecithins", Bernard F. Sauhuaj et al, American Oil Chemists' Society, 1985.
"Korrosionsschultz Durch Beschichtungsstoffe", Hanser Verlag, Oberflachenvorbereitung, 1980, pp. 246–248.
"Microbial Growth and Survival in Extremes of Environment", G. W. Gould et al., Academic Pres, 1980.
"Bacterial Adherence", E. H. Beachey, Chapman and Hall, 1980.
"Bacterial Adhesion, Mechanisms and Physiological Significance", by Dwayne C. Savagae et al., Plenum Press, 1985.
"Bacterial Adhesins", K. Jann et al., Springer–Verlag, 1990.
"Liposomes: Preparation Characterization and Preservation", D. Lichtenberg et al, Methods of Biochemical Analysis, vol. 33, pp. 337–462, Wiley, 1988.
"Petroleum Microbiology", Ronald M. Atlas, MacMillan, 1984.
"Enhanced Biodegradation of Pesticides in the Environment", Kenneth D. Racke et al., American Chemical Society, 1990.
"Preparation of Liposomes", Roger R. C. New, Liposomes: A Practical Approach, IRL Press, Oxford, 1990.
"Stability and Phase Behavior of Mixed Surfactant Vesicles", S. A. Safran et al, The American Physical Society, 1991.
"Evidence From Liposome Encapsulation for Transport-Limited Microbial Metabolism of Solid Alkanes", Applied and Environmental Microbiology, vol. 55, No. 2, Feb. 1989, Miller et al., pp. 269–274.
"Liposomal Solution for Microbial Catalysis in Organic Solvents?", Trends in Biotechnology, vol. 6, No. 1, Jan. 1988, pp. 1–2.
"In Situ Biorestoration of Organic Contaminants in the Subsurface", Environmental Science and Technology, vol. 23, No. 7, Jul. 1989, pp. 760–766.

*Primary Examiner*—Thomas G. Wyse
*Attorney, Agent, or Firm*—Lowe, Price, LeBlanc & Becker

[57] ABSTRACT

The invention provides a moist, absorbent material for cleaning articles and surfaces, wherein the material is moistened with an aqueous solution containing liposomes having vesicles of a diameter of up to about 100 nm.

9 Claims, No Drawings

MOIST, ABSORBENT MATERIAL FOR CLEANING ARTICLES AND SURFACES

The present specification is a continuation-in-part of U.S. Ser. No. 08/013,846, filed on Feb. 5, 1993, U.S. Pat. No. 5,376,183 entitled, "Method for Cleaning Industrial and Domestic Articles and Surfaces Contaminated with Organic or Lipophilic Wastes," now allowed, which in turn is a continuation-in-part of U.S. Ser. No. 07/653,319, filed Feb. 11, 1991, U.S. Pat. No. 5,401,413 and entitled "Method and Composition for Enhancing the Biodegradation of Biodegradable Organic Wastes," also now allowed.

The present invention relates to a moist, absorbent material for cleaning articles and surfaces. More particularly, the present invention relates to a moist, absorbent material, and especially a moist towelette, for cleaning articles and surfaces by applying liposomes thereto.

Prior research and patents have been directed to enhanced oil recovery using modified liposomes.

Thus, e.g., in U.S. Pat. No. 4,811,791 there is described and claimed a method of recovering a petroleum from an underground source thereof, comprising injecting into said underground source a petroleum displacement agent comprising a fluid and a modified liposome, said liposome being present in an amount sufficient to lower the interfacial tension between said fluid and said petroleum to below about 50 millidynes. Said patent, however, was limited to the recovery of petroleum from an underground source.

U.S. patent application Ser. No. 07/653,319, the teachings of which are incorporated herein by reference, provides a method for readily cleaning up sites contaminated with hydrocarbons which can be carried out efficiently without effecting the ecology and at relatively low costs.

According to the invention, it was found, as described hereinafter, that liposomes modify the physical properties of oil and the organic and lipophilic wastes by increasing the polarity and wettability thereof.

Phospholipids, which are the raw materials from which the liposomes used in the present invention are prepared, are naturally occurring membrane-lipids in which glycerol is linked to two long chain fatty acids, a phosphoric acid residue and a nitrogen-containing base (e.g. choline). While most phospholipids of animal origin have one saturated and one unsaturated fatty acid, plants (e.g. soybean) supply phospholipids having mostly two polyunsaturated fatty acids. For large scale application of liposomal phospholipids for environmental aspects, availability and a low cost are two major prerequisites. Plant phospholipids fulfill both requirements: their potential yield is more than half-a-million tons per year and, as by-products of the edible oil industry; they are being used for animal feed.

Liposomes for use in the absorbent materials of the present invention can be prepared from phospholipids, which may be supplied in a dry state or in a solution of phospholipid in an organic solvent which is either immiscible with water (e.g., ether, alkylhalides etc.) or miscible with water (e.g., alcohols, dimethylsulfoxide etc).

Numerous methodologies have been developed for preparation of liposomes; they can be prepared in various sizes and number of lamellae. For use in the absorbent materials of the present invention, unilamellar liposomes are preferred.

The preparation of small unilamellar liposomal vesicles on a small scale can be achieved by ultrasonic irradiation or extrusion of hydrated phospholipids. For large scale preparation, phospholipids are hydrated by mechanical shaking of dry phospholipids in water or water-containing salts. The multilamellar liposomes thus formed are then homogenized in high-pressure dairy homogenizers. Using this approach, small, unilamellar vesicles of natural or modified soybean phosphatides of less than 100 nm in diameter were produced, which were stable to storage at room temperature in water and resisted aggregation or fusion for at least two years.

As stated above, it has now been found that these unilamellar liposomes modify the physical properties of organic and lipophilic wastes to increase the polarity and wettability thereof.

In a further aspect of the present invention, as described and claimed in U.S. Ser. No. 08/013,846, the teachings of which are also incorporated herein by reference, it was found that absorbents can be used for cleaning industrial and domestic surfaces and articles contaminated with organic or lipophilic wastes.

In a still further aspect of the present invention, it has now been found that absorbents can be incorporated into absorbent materials such as cotton balls, cotton swabs and moist towelettes, having a multitude of uses for cleaning various articles and surfaces.

Moist towelettes having varied compositions and applications are well-known.

Originally, moist towelettes were available in individual, sealed aluminum packets for freshening up and cleaning hands in situations where water was not readily available, such as on airplane flights, hiking expeditions, etc.

A further development involved the preparation of a package of a plurality of larger moist towelettes, individually removable from a semi-sealed container, for bathroom use as well as for baby care.

Thus, e.g., Scott Paper Company manufactures and markets a moist towelette under the trademark Baby Fresh®, which is listed as containing the following ingredients: purified water, propylene glycol, PEG 75, lanolin, cocoamphodiacetate, polysorbate 20 for cleaning and moisturizing, as well as methylparaben, propylparaben, 2-bromo-2-nitro-propane-1,3-diol and fragrance, for freshness and fragrance.

Another product, manufactured and sold in Israel, lists as its ingredients: water, lanolin, amphoteric-6, Tween-20, propylene glycol, fragrance, and EDTA.

As will be noted, both of these and similar products are based on a combination of water, propylene glycol and surfactants to achieve the cleaning effect.

In contradistinction to such known moist towelettes, according to the present invention there is now provided a moist towelette for cleaning articles and surfaces, wherein said towelette is moistened with an aqueous solution containing liposomes having vesicles of a diameter of up to about 100 nm.

Cotton swabs, i.e., a small ball of cotton at either or both ends of a stick, have been available for decades, the most popular product being the Q-Tips® produced by Johnson & Johnson. Heretofore, however, all of the cotton swab products on the market are dry swabs, which can cause irritation to the ear or nose cavity when applied thereto.

It has now been found that by pre-soaking said cotton swabs in a liposome solution according to the present invention, there are produced pre-moistened swabs having improved properties.

The absorbent material of the present invention can be prepared to contain varying concentrations of liposomes, depending on their intended use. As described hereinafter, suspensions, dispersions, and even gels of liposomes in aqueous solution, can be prepared, limited only by the saturation point of the solution. Thus, in preferred embodiments of the present invention, said absorbent material is moistened with an aqueous solution containing between about 0.01–60% by weight liposomes in water.

In especially preferred embodiments of the present invention, said absorbent material is moistened with an aqueous solution containing between about 0.05–25% by weight liposomes in water.

Furthermore, said liposomes can be introduced into towelettes made of non-woven fabric such as cotton, viscose, viscose polyester or viscose polyethylene; paper, or woven fabric.

Because of the special and unique properties of the liposomes used in the present invention, the moist towelettes containing the same can be used not only for the traditional uses of personal hygiene and baby care, but can also be used for cleaning articles and surfaces contaminated with organic and/or lipophilic deposits, to increase the polarity and wettability thereof, thereby facilitating the removal of said deposits and cleaning said articles and surfaces.

Furthermore, the moist towelettes of the present invention are effective for cleaning grease and grime deposits from domestic and industrial articles and surfaces.

In a further aspect of the present invention, it has been found that the liposomes of the present invention can be combined with a disinfectant such as chlorohexidine gluconate, cetramide, benzylknium chloride or peptides such as polymixin B, to produce a moist towelette having disinfectant properties, which could be used, e.g., for cleaning the teats of cows before milking, as well as for producing absorbent material of various configurations for female hygenic use.

In contradistinction to the detergents presently used today in commercial liquid cleansers, which must be rinsed off the articles or surfaces to be cleaned, the towelettes of the present invention leave a desirable, protective, thin layer. Furthermore, said protective layer, when deposited on a glass surface, has been found to possess a water-repellant effect, as exemplified hereinafter.

As discussed herein, the preferred liposomes of the present invention have vesicles of a diameter of up to 100 nm and vesicles having a diameter of about 20–80 nm are especially preferred. Similarly, said liposomes are preferably phospholipid liposomes.

In U.S. Pat. Nos. 4,230,562 and 4,414,333 there are described methods and compositions for depolluting fresh water and salt water bodies from crude oil, petroleum products and salt water bodies from crude oil, petroleum products and their derivatives, which include, inter alia, providing lecithin as a phosphorous source. However, as indicated hereinbefore, for rapid and efficient conversion of a phospholipid source such as lecithin into the structural form of small unilamellar liposomes having the desired properties of modifying polarity and wettability of organic wastes for use in the methods of the present invention, it is necessary to subject the same to ultrasonic irridation, extrusion or similar processes. Therefore, neither of these patents teaches or suggests the preparation and use of the towelettes of the present invention.

In U.S. Pat. No. 5,019,174 there is described a lipid vesicle skin cleaner and a method for removing oil from a surface using the same through liposomal encapsulation. As will be noted, however, said patent is directed to, and limited to, the use of paucilamellar lipid vesicles which are broken or fractured and reformed, thereby encapsulating the oil present on said surface.

In contradistinction to the teachings of said patent, the present invention utilizes liposomes which modify the physical properties of organic and lipophilic deposits to increase the polarity and wettability thereof, thereby facilitating their removal from surfaces on which they are found. Thus, in the present invention, small vesicles, i.e., those having a diameter of about 20–80 nm, were found to be especially effective; this is the opposite from what would be expected from the teaching of said patent, since the encapsulated volume is inversely proportional to the liposomal size.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1A

Ten grams of soy bean lecithin are dispersed in 100 ml distilled water, followed by 5 minutes of high-pressure homogenization at 10,000 psi. The liposomes formed are mostly unilamellar <100 nm.

EXAMPLE 1B

The liposomes of Example 1A are added to a small container, in which 4.5 meters of non-woven viscose (13.5 cm wide) was placed. The viscose is pre-divided into 200 equal pieces, which are still attached to each other. The container is sealed and stored until all the liposome suspension is adsorbed by the viscose. These fabric pieces are used for cleaning, as described in the examples given below.

EXAMPLE 2

15 grams of egg lecithin containing 0.2 mole % of Vitamin E antioxidant are dissolved in 30 ml of chloroform; the solvent is removed by flash evaporation. Other antioxidants used in parallel liposomal preparations include butylated hydroxy toluene (BHT), butylated hydroxy anisole (BHA), and Oxynex 2003. Large multilamellar liposomes are prepared by adding 100 ml of distilled water containing EDTA chelator, and shaking the aqueous solution with the thin lipid layer. Down-sizing of the liposomes to a size smaller than 100 nm is achieved by serial extrusion of the multilamellar liposomes through a series of polycarbonate filters, starting with a pore size of 600 nm, and ending with a pore size of 50 nm. The pressure is adapted to the filter pore size. The last step of extrusion, through the 50 nm pore size filter, is repeated three times. All liposomes formed are smaller than 100 nm, and are unilamellar. These liposomes are used to moisturize viscose fabric, as described above in Example 1B.

EXAMPLE 3

100 grams of soybean lecithin are dispersed in 1.0 liter of distilled water, using a high shearing homogenizer. A paraban preservative is added at bacteriostatic concentration. Liposome down-sizing is performed, using high pressure homogenization as described above in Example 1, to give liposomes having a size smaller than 100 nm. This liposome suspension is divided into 10 aliquots of 100 ml each.

EXAMPLE 4

100 ml of the liposome dispersion prepared in Example 3 are used to moisturize a woven fabric as described in Example 1, and used for cleaning of all parts of the human body.

EXAMPLE 5

100 ml of the liposome dispersion described in Example 3 are used to moisturize paper towelettes.

EXAMPLE 6

A gum, such as sodium alginate, Acacia, or Chondrus, is added to 100 ml of the liposome dispersion prepared in Example 3, and then applied to either woven or non-woven fabric, as described in Example 1B.

EXAMPLE 7

A thickening agent, such as carboxy methol cellulose (CMC) polyvinyl pyrolidone (PVP) or Veegum K is added to the liposomal dispersion prepared in Example 3, to obtain the desirable viscosity. The liposomal dispersion is then applied to woven or non-woven fabric, as described in Example 1B.

EXAMPLE 8A

Preparation of liposome moisturized tissue for facial or body use: 10 grams of soybean lecithin are dissolved in 50 ml of ethanol, together with an antioxidant as in Example 2 and a preservative as in Example 3, and the addition of rose extract for cleaning and tonic, camphor extract for skin stimulation and comfort and Chamomile extract for soothing. The ethanolic solution is injected at a rate of 0.1 ml per minute into 1 liter of stirred, bi-distilled water.

EXAMPLE 8B

The liposomes formed in Example 8A are of a size smaller than 100 nm, and are used to moisturize either woven or non-woven fabric, as described in Example 1B. These fabrics are used as described in the following examples.

EXAMPLE 9A

Preparation of liposome moisturized tissue containing collagen and elastin: 100 ml of small, unilamellar, 10% soybean lecithin liposomes, having a size <50 nm, are prepared in bi-distilled water. These liposomes are colyophilized with a 100 ml solution containing a mixture of collagen and elastin at protein concentration in the range of 0.05 to 2.0%. The dry powder is dispersed in a final volume of 100 ml water or buffer at the desired pH. The multilamellar liposomes formed are down-sized, either by high-pressure homogenization as described in Example 1A, or by serial extrusion, as described in Example 2.

EXAMPLE 9B

The liposomes formed in Example 9A are of a size smaller than 100 nm, and are used to moisturize either woven or non-woven fabric, as described in Example 1B. These fabrics are used as described in the following examples.

EXAMPLE 10

Preparation of liposome-moisturized tissue for cleaning and disinfecting: Liposomes smaller than 100 nm are prepared, as described in either Example 1A, 2, 3, 8A, or 9A, except that a disinfectant, selected from the group consisting of chlorhexidine gluconate, cetramide, benzylknium chloride and peptides such as polymixin B, which have a high affinity to liposomes, is added to either the ethanol or aqueous phase, to give the optimal concentration for antiseptic activity.

EXAMPLE 11

Preparation of liposome-moisturized tissue for soothing and local anesthetic: Liposome-moisturized fabric is prepared as described in Example 10, with the addition of a local anesthetic selected from benzocaine and tetracaine to either the water or the ethanol.

EXAMPLE 12

Liposome dispersions are prepared as described above in Examples 1A, 2, 3, 8A and 9A, and then various types of cloth, made of either synthetic or natural fibers, are moisturized with the liposomal dispersion in a sealed container.

EXAMPLE 13

Liposome dispersions are prepared as described in Examples 1A, 2, 3, 8A and 9A, and are used to moisturize cotton balls enclosed in a sealable container.

EXAMPLE 14

The cotton ends of "cotton tips" are moisturized with liposome dispersions prepared as described in Examples 1A, 2, 3, 8A and 9A, in a sealable container. These tips are used to clean human or animal ears.

EXAMPLE 15

Sterile liposome dispersions are prepared as in Examples 1A, 2, 3, 8A and 9A and are used to moisturize tampons of various kinds and sizes. Each of the tampons is sealed in a separate envelope, which prevents evaporation and preserves its sterility.

EXAMPLE 16

Liposome dispersions are prepared as described in Examples 1A, 2, 3, 8A and 9A, in a buffer of neutral pH. They are used to moisturize 5-cm diameter pads of woven or non-woven fabric in a sealed container. These pads are used for removal of make-up from the eyes and face.

EXAMPLE 17

Liposome dispersions are prepared as described in Examples 1A, 2, 3, 8A and 9A, and are used to moisturize woven or non-woven fabric, as described in Example 1B. The container is attached to a vacuum pump and part of the water which moisturizes the fabric is removed by vacuum, to achieve the desirable weight % of lipids in the water in the range of 0.01–60% . Then the containers are sealed.

EXAMPLE 18

Liposome dispersions are prepared as described in Examples 1A, 2, 3, 8A and 9A. These dispersions are diluted to the desired lipid concentration, in the range of 25 to 0.05%, and then applied to woven or non-woven fabric towelettes, cotton balls, or cotton tip swabs, and then stored in sealed containers.

EXAMPLE 19

Liposome dispersions are prepared and diluted as described in Example 18, and then used to moisturize tampons as described in Example 15.

EXAMPLE 20

A non-woven fabric was moistened with an aqueous solution containing 1% liposomes, to form a moist towelette. The towelette was applied to remove eye makeup. The makeup was totally removed and the skin was left clean, moist and soft.

EXAMPLE 21

A non-woven tissue was moistened with an aqueous solution containing 0.1% liposomes, to form a moist towelette. The towelette was applied to clean eyeglass lenses. The lenses were left clean, without any scratches.

EXAMPLE 22

A woven cloth was moistened with an aqueous solution containing 17% liposomes, to form a moist towelette. The towelette was applied to clean the greasy hands of a garage mechanic, leaving his hands clean and moisturized.

EXAMPLE 23

A paper towelette was moistened with an aqueous solution containing 0.2% liposomes. The towelette was used to clean computer and television screens. Both screens were left clean, without any scratches, and without any generation of static electricity.

EXAMPLE 24

A non-woven fabric was moisturized with an aqueous solution containing 0.5% liposomes, to form a moist towelette. The towelette was applied to clean the windshield of a motorcyclist's helmet. When driving through a heavy rain, the liposomes on the windshield repelled the drops of water, leaving a clear view to the cyclist.

EXAMPLE 25

A non-woven fabric was moisturized with an aqueous solution containing 0.5% liposomes, to form a moist towelette. The towelette was applied to clean a baby's behind. The skin was left clean and soft, without any apparent irritation.

EXAMPLE 26

A non-woven fabric was moisturized with an aqueous solution containing 0.5% liposomes, to form a moist towelette. The towelette was used to wet a thick layer (about 2 mm) of soot covering the interior (burner and burning chamber) of a Delville kerosene heater. Five minutes after this application, the soot was wiped with a cloth slightly wetted with water, resulting in complete removal of the soot and leaving the metal entirely clean. In a parallel experiment in which the soot was treated with a cloth wetted with water (instead of the liposomes), wiping with a set cloth removed only a small portion of the soot, most of which remain adhered to the metal of the burner and chamber.

EXAMPLE 27

Soot from the above-mentioned burner which fell on the floor (made of ceramic tiles) was wiped with a moist towelette containing 0.5% liposomes, resulting in complete removal of the soot and cleanup of the floor. In parallel, wetting the soot with water only and wiping with a paper tissue removed only a small portion of the soot from the floor.

EXAMPLE 28

A non-woven fabric was moisturized with an aqueous solution containing 0.5% liposomes, to form a moist towelette. The towelette was used to wipe one-half of the front windshield of a car on the driver's side.

The car was driven through a relatively heavy rain at 90 kph. Watching the road through the liposome portion of the windshield did not require the use of windshield wipers. The raindrops were observed to be repelled from the windshield, leaving tiny small drops.

The rest of the windshield was completely covered with a heavy film of water, which prevented the ability to see the road clearly enough to drive.

EXAMPLE 29

Fifty sheets of non-woven tissues, having a size of 200× 140 mm, were prepared. The sheets were placed in a container measuring 205×145 60 mm. An aqueous solution of 5% liposomes was prepared according to Example 1A, and 150 ml of this solution were poured into the container until all of the tissues were evenly soaked, and the container was closed. The moistened towelettes were then individually removed from said container as needed, and used to clean counter and table surfaces in a kitchen area, whereby grease, grime and food deposits were readily removed.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A moist, absorbent material for cleaning articles and surfaces, wherein said material is moistened with an aqueous solution containing unilamellar liposomes having vesicles of a diameter of up to about 100 nm.

2. A moist, absorbent material according to claim 1, wherein said material is a non-woven fabric.

3. A moist, absorbent material according to claim 1, wherein said material is a woven fabric.

4. A moist, absorbent material according to claim 1, wherein said material is a towelette.

5. A moist, absorbent material according to claim 1, wherein said material is a cotton tip swab.

6. A moist, absorbent material according to claim 1, further comprising a disinfectant incorporated therein.

7. A moist, absorbent material according to claim 1, wherein said liposomes have vesicles of a diameter of about 20–80 nm.

8. A moist, absorbent material according to claim 1, wherein said liposomes are phospholipid liposomes.

9. A moist, absorbent material according to claim 1 for cleaning organic and lipophilic deposits from articles and surfaces, wherein said liposomes modify the physical properties of said deposits to increase the polarity and wettability thereof, thereby facilitating the removal of said deposits and cleaning said articles and surfaces.

* * * * *